United States Patent
Gladden et al.

(10) Patent No.: US 10,934,568 B2
(45) Date of Patent: Mar. 2, 2021

(54) CONVERSION OF SUGARS TO IONIC LIQUIDS

(71) Applicant: NATIONAL TECHNOLOGY & ENGINEERING SOLUTIONS OF SANDIA, LLC, Albuquerque, NM (US)

(72) Inventors: John M. Gladden, Alameda, CA (US); Tanmoy Dutta, Berkeley, CA (US); Jian Sun, Albany, CA (US); Seema Singh, Clarksburg, MD (US); Blake A. Simmons, San Francisco, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 16/308,440

(22) PCT Filed: Jun. 7, 2017

(86) PCT No.: PCT/US2017/036438
§ 371 (c)(1),
(2) Date: Dec. 7, 2018

(87) PCT Pub. No.: WO2017/214332
PCT Pub. Date: Dec. 14, 2017

(65) Prior Publication Data
US 2019/0136281 A1    May 9, 2019

Related U.S. Application Data

(60) Provisional application No. 62/346,955, filed on Jun. 7, 2016.

(51) Int. Cl.
| | |
|---|---|
| *C12P 19/14* | (2006.01) |
| *C07H 3/02* | (2006.01) |
| *C07H 3/06* | (2006.01) |
| *C12P 19/02* | (2006.01) |
| *C07H 1/00* | (2006.01) |

(52) U.S. Cl.
CPC ............. *C12P 19/14* (2013.01); *C07H 1/00* (2013.01); *C07H 3/02* (2013.01); *C07H 3/06* (2013.01); *C12P 19/02* (2013.01); *C12P 2201/00* (2013.01); *C12Y 302/01021* (2013.01); *C12Y 302/01032* (2013.01)

(58) Field of Classification Search
CPC .................................................... C12P 19/02
See application file for complete search history.

(56) References Cited

U.S. PATENT DOCUMENTS

| | | |
|---|---|---|
| 4,865,973 A | 9/1989 | Kollerup et al. |
| 8,187,489 B1 | 5/2012 | Davis |
| 2011/0247494 A1 | 10/2011 | Dinnage et al. |
| 2012/0301948 A1 | 11/2012 | Brennan et al. |
| 2014/0004563 A1 | 1/2014 | Paripati et al. |
| 2014/0220651 A1 | 8/2014 | Raines et al. |
| 2016/0122379 A1 | 5/2016 | Singh et al. |

FOREIGN PATENT DOCUMENTS

| | | |
|---|---|---|
| CN | 100355737 | 12/2007 |
| WO | 2016/070125 A1 | 5/2016 |

OTHER PUBLICATIONS

Boissou et al., "Transition of cellulose crystalline structure in biodegradable mixtures of renewably-sourced levulinate alkyl ammonium ionic liquids, γ-valerolactone and water," Green Chem., 2014, 16, 2463-2471.
Huang et al., "A review of separation technologies in current and future biorefineries," Separation and Purification Technology, 2008, 62, 1-21.
Liu et al., "MEP pathway-mediated isopentenol production in metabolically engineered *Escherichia coli*", Microbial Cell Factories, vol. 13, Article 135, Sep. 12, 2014, 7 pages.
Liu et al., "Ionic liquids from renewable biomaterials: synthesis, characterization and application in the pretreatement of biomass," Green Chem, 2012, 14, 304-307.
Shi et al., "One-pot ionic liquid pretreatment and saccharification of switchgrass," Green Chem., 2013, 15, 2579-2589.
Sun et al., "Understanding pretreatment efficacy of four cholinium and imidazolium ionic liquids by chemistry and computation," Green Chem., 2014, 16, 2546-2557.

*Primary Examiner* — Bin Shen
(74) *Attorney, Agent, or Firm* — Kilpatrick Townsend & Stockton LLP (57) ABSTRACT

Disclosed herein are methods for preparing sugar compositions. The methods include: i) forming a mixture including polysaccharide biomass and an ionic liquid solution, wherein the ionic liquid solution contains water and an ionic liquid, and the ionic liquid contains a) a cation and b) a sugar acid anion or a ketoacid anion; ii) maintaining the mixture under conditions sufficient to dissolve at least a portion of the polysaccharide present in the polysaccharide biomass; iii) adding at least one glycoside hydrolase to the mixture; and iv) maintaining the mixture containing the glycoside hydrolase under conditions sufficient to hydrolyze at least a portion of the dissolved polysaccharide, thereby forming the sugar compositions. The sugar compositions contain at least one monosaccharide or oligosaccharide. New sugar-based ionic liquids are also described.

14 Claims, 1 Drawing Sheet

CONVERSION OF SUGARS TO IONIC LIQUIDS

CROSS REFERENCES TO RELATED APPLICATIONS

The present application is a U.S. National Phase of International Application No. PCT/US2017/036438, filed Jun. 7, 2017, which claims priority to U.S. Provisional Pat. Appl. No. 62/346,955, filed Jun. 7, 2016, which is incorporated herein by reference in its entirety.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the United States Department of Energy. The government has certain rights in the invention.

BACKGROUND OF THE INVENTION

In recent years, tremendous efforts have been made to develop biofuels made from lignocellulosic biomass, which is derived from agricultural wastes, forest residues, and dedicated energy crops. However, one of the greatest limitations facing the economic viability of this technology is the recalcitrant nature of the lignocellulosic biomass to enzymatic hydrolysis into its component sugars. This resistance to breakdown necessitates the use of pretreatment steps to enhance the accessibility to and hydrolysis of the carbohydrate components present in the lignocellulosic biomass. Most pretreatment processes are thenno-chemical processes that utilize combinations of high temperatures and pressures, or dilute acids or alkalis, to open up the structure of the biomass. Such processes necessitate the use of specialized equipment and high-energy inputs.

Ionic liquids (ILs) have come into prominence over recent years and have been used as innovative fluids for chemical processing. They are known as environmentally friendly solvents primarily due to their low volatility and their potential recyclability. Recently, the use of ILs for the pretreatment of biomass has been shown to be a promising technology, allowing for the solubilization of crystalline cellulose and biomass under relatively mild conditions. Reconstitution of the biomass from the IL results in an amorphous product that significantly increases the rate of enzymatic hydrolysis to its component soluble sugars. For instance, the IL 1-ethyl-3-methylimidazolium acetate [$C_2$Mim][OAc] has been found to be effective at the dissolution of biomass and the subsequent enhancement of enzymatic hydrolysis (also termed saccharification).

The ionic liquid pretreatment process can generally be described as the dissolution of biomass into the ionic liquid at an elevated temperature with stirring, followed by the optional addition of a precipitant (or, alternatively, an anti-solvent) that precipitates the biomass from solution. This precipitant or anti-solvent is typically either water or ethanol, or some other solvent with hydrogen bonding capacity. Once the biomass has been precipitated, solid/liquid separation and downstream enzymatic hydrolysis of the now amorphous biomass results in monosaccharides suitable for fermentation. Typically, the ionic liquid pretreatment process employs atmospheric pressure and temperatures ranging from about 120° C. to 160° C. Recycling of ionic liquid can be achieved by distillation of the precipitating solvent.

Although pretreatment with ionic liquids has met with success, ionic liquids are expensive and the pretreatment process is both energy and time intensive. Furthermore, ionic liquids can destabilize cellulases used for hydrolysis and inhibit the growth of microorganisms used for subsequent fermentation of the component soluble sugars. As such, what is needed are methods for processing biomass in which pretreatment, hydrolysis, and fermentation steps are compatible with each other. Use of ionic liquids that are renewably sourced and non-toxic are particularly desired. The present invention provides methods that fulfill these and other needs.

BRIEF SUMMARY OF THE INVENTION

Exemplary embodiments provided in accordance with the presently disclosed subject matter include, but are not limited to, the claims and the following embodiments:

1. A method for preparing a sugar composition, the method comprising:
   i) forming a mixture comprising polysaccharide biomass and an ionic liquid solution, wherein
      the ionic liquid solution comprises water and an ionic liquid, and
      the ionic liquid comprises a) a cation and b) a sugar acid anion or a ketoacid anion;
   ii) maintaining the mixture under conditions sufficient to dissolve at least a portion of the polysaccharide present in the polysaccharide biomass;
   iii) adding at least one glycoside hydrolase to the mixture; and
   iv) maintaining the mixture containing the glycoside hydrolase under conditions sufficient to hydrolyze at least a portion of the dissolved polysaccharide, thereby forming the sugar composition;
   wherein the sugar composition comprises at least one monosaccharide or oligosaccharide.

2. The method of embodiment 1, wherein the sugar acid is selected from the group consisting of an aldaric acid, an aldonic acid, a uronic acid, and combinations thereof.

3. The method of embodiment 1 or embodiment 2, wherein the sugar acid is selected from the group consisting of mucic acid, saccharic acid, xylaric acid, arabinaric acid, and mannaric acid.

4. The method of embodiment 1, wherein the ketoacid is selected from the group consisting of α-ketoglutaric acid, pyruvic acid, and levulinic acid.

5. The method of embodiment 1, wherein the anion is selected from the group consisting of a mucic acid anion, a mucic acid dianion, an α-ketoglutaric acid anion, and an α-ketoglutaric acid dianion.

6. The method of any one embodiments 1-5, wherein the cation is selected from choline, $(C_{1-18}$ alkyl$)_3$NH$^+$, $(C_{1-6}$ alkyl$)_x(C_{6-18}$ alkyl$)_y$N$^+$, $(C_{1-10}$ alkyl$)_z$imidazolium, $(C_{1-10}$ alkyl)$_z$pyrazolium, and mixtures thereof; wherein subscript x and subscript y are each 0, 1, 2, 3, or 4, and the sum of x and y is 4; and wherein each subscript z is 1, 2, or 3.

7. The method of embodiment 6, wherein the cation is choline.

8. The method of embodiment 6, wherein the cation is selected from 1-ethyl-3-methylimidazolium, 1-butyl-3-methylimidazolium, 1-ethyl-2,3-dimethylimidazolium, tris(2-hydroxyethyl)methylammonium, 1-methylimidazolium, 1,2,4-trimethylpyrazolium, triethylammonium, tributylmethylammonium, hexadecyltrimethylammonium, myristyltrimethylammonium, tridodecylmethylammonium, trimethyloctadecylammonium, and choline.
9. The method of any one of embodiments 1-8, wherein the ionic liquid solution comprises from about 25% w/w) to about 95% (w/w) water.
10. The method of embodiment 1, wherein the ionic liquid solution comprises 50-90% (w/w) water; and further comprises 10-50% dicholine mucate (w/w) or 10-50% dicholine α-ketoglutarate (w/w).
11. The method of any one of embodiments 1-10, wherein the mixture in step i) comprises from about 5% (w/w) to about 30% (w/w) polysaccharide biomass.
12. The method of any one of embodiments 1-11, wherein step ii) comprises maintaining the mixture of step i) at a temperature of at least about 100° C. for at least about 30 minutes.
13. The method of any one of embodiments 1-12, wherein the pH of the mixture in step i) is greater than 7.
14. The method of embodiment 13, further comprising:
ii-b) reducing the pH of the mixture containing the dissolved polysaccharide to less than 7 prior to adding the glycoside hydrolase in step iii).
15. The method of embodiment 14, wherein step ii-b) comprises adding an acid to the mixture resulting from step ii).
16. The method of embodiment 15, wherein the acid used in step ii-b) is the same sugar acid or ketoacid used in step i).
17. The method of embodiment 15 or embodiment 16, wherein the molar amount of acid in step ii-b) is equal to the molar amount of the sugar acid or ketoacid in step i).
18. The method of any one of embodiments 15-17, wherein step ii-b) comprises adding an acid to the mixture resulting from step ii); wherein the acid used in step ii-b) is the same sugar acid or ketoacid used in step i); and wherein the molar amount of acid in step ii-b) is equal to the molar amount of the sugar acid or ketoacid in step i).
19. The method of embodiment 1, wherein the polysaccharide biomass comprises cellulose, hemicellulose, lignocellulose, or mixtures thereof.
20. The method of embodiment 19, wherein the polysaccharide biomass comprises lignocellulose.
21. The method of any one of embodiments 1-20, wherein the polysaccharide biomass is derived from corn stover, corn fiber, hardwood, softwood, cereal straw, switchgrass, Miscanthus, rice hulls, municipal solid waste (MSW), industrial organic waste, office paper, or mixtures thereof.
22. The method of any one of embodiments 1-21, wherein the glycoside hydrolase is a cellulase.
23. The method of any one of the preceding embodiments 1-22, wherein the glycoside hydrolase is selected from the group consisting of an endoglucanase, an exoglucanase, a β-glucosidase, a xylanase, and mixtures thereof.
24. An ionic liquid comprising at least one sugar acid anion and at least one cation, wherein the anion is selected from the group consisting of a sugar acid anion and a ketoacid ion.
25. The ionic liquid of embodiment 24, wherein the sugar acid is selected from the group consisting of an aldaric acid, an aldonic acid, a uronic acid, or a combination thereof.
26. The ionic liquid of embodiment 24 or embodiment 25, wherein the sugar acid is selected from the group consisting of mucic acid, saccharic acid, xylaric acid, arabinaric acid, and mannaric acid.
27. The ionic liquid of claim 24, wherein the ketoacid is selected from the group consisting of α-ketoglutaric acid, pyruvic acid, and levulinic acid.
28. The ionic liquid of any one of embodiments 24-27, wherein the anion is selected from the group consisting of a mucic acid anion, a mucic acid anion, an α-ketoglutaric acid anion, and an α-ketoglutaric acid dianion.
29. The ionic liquid of any one of embodiment 24-28, wherein the cation is selected from choline, $(C_{1-18}$ alkyl$)_3$NH$^+$, $(C_{1-6}$ alkyl$)_x$$(C_{6-18}$ alkyl$)_y$N$^+$, $(C_{1-10}$ alkyl$)_z$imidazolium, $(C_{1-10}$ alkyl$)_z$pyrazolium, and mixtures thereof; wherein subscript x and subscript y are each 0, 1, 2, 3, or 4, and the sum of x and y is 4; and wherein each subscript z is 1, 2, or 3.
30. The ionic liquid of embodiment 29, wherein the cation is choline.

DETAILED DESCRIPTION OF THE INVENTION

The present invention provides for a composition comprising an ionic liquid (IL) derived from a sugar, such as an aldaric acid converted from sugar. In some embodiments, the composition comprises a mixture of ILs derived from a sugar or sugars. In some embodiments, the sugar is derived from pretreatment and/or saccharification of biomass.

Sugars derived from lignocellulose can be converted into ILs by derivitization into aldaric acids. A variety of sugar-derived anions and cations can be used to form ILs that can be used for efficient biomass pretreatment.

The present invention provides for a method to convert a monomeric sugar into ionic liquid anions and/or cations. In some embodiments the method comprises converting a mixture of monomeric sugars into ionic liquid anions and/or cations. The monomeric sugars can be derived from lignocellulosic biomass hydrolysates rich in glucose and xylose or from any other sugar present in biomass, such as galactose, arabinose, mannose, or the like, or a mixture thereof. In some embodiments, the monomeric sugar is a $C_6$ sugar or a $C_5$ sugar, or a mixture thereof. In some embodiments, the monomeric sugar is a glucose, xylose, galactose, arabinose, mannose, or the like, or a mixture thereof.

To generate anions, a sugar can be chemically or enzymatically converted to its uronic, aldonic, or aldaric acid form. These anions can be paired with other non-sugar derived IL cations, such as choline, 1-ethyl-3-methylimidazolium, or the like, or with suaar cations generated by forming positively charged salts, using processes such as amination. It is demonstrated that the aldaric acid of galactose, mucic acid, can form an IL that is effective at pretreating lignocellulosic biomass when paired with a choline cation. A 36 wt. % choline; mucic acid IL generated from a mixture of choline hydroxide and mucic acid titrated to a pH of 13 is used to pretreat switchgrass at 140° C. for 1 hr, then the pH was adjusted to pH 5 and the IL concentration to 20%. This slurry is then enzymatically hydrolyzed with a commercial cellulase cocktail at 10 mg enzyme/g glucan and liberated 76% glucose and 49% xylose.

The process can be used in lignocellulosic biorefineries. Lignocellulosic biomass is pretreated and hydrolyzed, producing a mixture of sugars primarily consisting of glucose and xylose. A portion of the hydrolysate can be removed and used to convert the glucose, xylose, or both into their respective sugar acids (e.g., aldaric acids and the like). A number of known processes can be used for converting the sugars to sugar acids as described, for example, in U.S. Pat. Appl, Pub Nos. US 2015/0065749, US 2012/0045804, and US 2008/0187984, as well as U.S. Pat. Nos. 7,982,031 and 6,518,419, which are incorporated herein by reference. These anions can then be paired with an IL cation, such as choline at high pH (≥10) in water and subsequently used to pretreat additional lignocellulosic biomass, or be sold for other purposes. Sugar-derived cations could also be generated as well and used to form ILs to be used for pretreatment or applications.

I. Definitions

As used herein, the term "sugar composition" refers to a mixture containing one or more monosaccharides, oligosaccharides, or combinations thereof. Sugar compositions prepared according to the methods of the invention are also referred to as "hydrolysates" in the present application.

As used herein, the term "monosaccharide" refers to a sugar having a five-membered carbon backbone (i.e., a pentose) or a six-membered carbon backbone (i.e., a hexose). Examples of monosaccharides include, but are not limited to, glucose, ribose, fucose, xylose, arabinose, galactose, mannose, glucuronic acid, and iduronic acid. Monosaccharides also include pentoses and hexoses substituted with hydroxy groups, oxo groups, amino groups, acetylamino groups, and other functional groups.

As used herein, the term "oligosaccharide" refers to a compound containing at least two sugars covalently linked together. Oligosaccharides include disaccharides, trisaccharides, tetrasaccharides, pentasaccharides, hexasaccharides, heptasaccharides, octasaccharides, and the like. Covalent linkages for linking sugars generally consist of glycosidic linkages (i.e., C—O—C bonds) formed from the hydroxyl groups of adjacent sugars. Linkages can occur between the 1-carbon (the anomeric carbon) and the 4-carbon of adjacent sugars (i.e., a 1-4 linkage), the 1-carbon (the anomeric carbon) and the 3-carbon of adjacent suaars (i.e., a 1-3 linkage), the 1-carbon (the anomeric carbon) and the 6-carbon of adjacent suaars (i.e., a 1-6 linkage), or the 1-carbon (the anomeric carbon) and the 2-carbon of adjacent sugars (i.e., a 1-2 linkage). Other linkages can be present in the oligosaccharide, depending on the particular sugar subunits present. Those of skill in the art will appreciate that a sugar can be linked within an oligosaccharide such that the glycosidic bond at the anomeric carbon is in the α- or β-configuration.

As used herein, the term "polysaccharide" generally refers to a compound containing 10 or more sugars linked together as described for oligosaccharides.

As used herein, the term "biomass" and "polysaccharide biomass" are used interchangeably to refer to plant-based material that includes a plurality of components such as lignin, cellulose, and hemicellulose. Sources of biomass includes trees, shrubs, grasses, wheat, wheat straw, sugar cane bagasse, corn, corn husks, corn kernel including fiber from kernels, products and by-products from milling of grains such as corn, rice, wheat, and barley, as well as municipal solid waste, waste paper, and yard waste. Biomass sources can also include herbaceous material, agricultural residues, forestry residues, and paper mill residues. Additional examples include branches, bushes, canes, corn and corn husks, energy crops, forests, fruits, flowers, grains, grasses, herbaceous crops, leaves, bark, needles, logs, roots, saplings, short rotation woody crops, shrubs, switchgrasses, trees, vegetables, fruit peels, vines, sugar beet pulp, wheat midlings, oat hulls, hard and soft woods, organic waste materials generated from agricultural processes including farming and forestry activities, or mixtures thereof.

As used herein, the term "lignocellulosic biomass" refers to natural and/or synthetic materials containing lignin, cellulose, and/or hemicellulose. Generally, these materials also contain (but need not contain) xylan, protein, and/or other carbohydrates, such as starch.

As used herein, the term "cellulose" refers to refers to a homopolymer of β(1→4) linked D-glucose units that form a linear chain. Cellulose can contain several hundred to several thousand or more glucose units, making cellulose a polysaccharide.

As used herein, the term "hemicellulose" refers to a heteropolymer containing different saccharide units, including but not limited to, xylose, mannose, galactose, rhamnose and arabinose. Hemicellulose forms a branched polymer with several hundred to several thousand sugar units. Hemicellulose can include both pentose and hexose sugars.

As use herein, the term "lignin" refers to a phenylpropane polymer of monolignol monomers (p-coumaryl alcohol, coniferyl alcohol, and sinapyl alcohol) found as an integral part of the secondary cell walls of plants and certain types of algae.

As used herein, the term "ionic liquid" refers to an organic salt that is a liquid at room temperature rather than a solid or crystalline substance. Ionic liquids typically exhibit a number of advantageous properties, including low volatility, thermal stability, and the ability to dissolve a wide range of solutes under mild conditions.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, test-butyl, pentyl, isopentyl, hexyl, etc. Alkyl can also refer to alkyl groups having up to 20 carbons atoms, such as, but not limited to heptyl, octyl, nonyl, decyl, etc. An "alkane" refers to the parent compound of the alkyl radicals described herein.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. An "alkene" refers to the parent compound of the alkenyl radicals described herein.

As used herein, the term "sugar acid" refers to a monosaccharide as described herein having at least one carboxy moiety (i.e., at least one —COOH group). As used herein, the term "sugar acid anion" refers to a sugar acid wherein at least one of the carboxy moieties is deprotonated (i.e., present as a —COO⁻ anion). Sugar acid anions are generally bound to cations in an ionic liquid via electrostatic interaction.

As used herein, the term "ketoacid" refers to a an alkane or alkene having at least one carboxy moiety and least one oxo moiety (i.e., at least one —COOH group and at least one C=O group). As used herein, the term "ketoacid anion" refers to a ketoacid wherein at least one of the carboxy moieties is deprotonated (i.e., present as a —COO⁻ anion). Ketoacid anions are generally bound to cations in an ionic liquid via electrostatic interaction.

As used herein, the term "cation" refers to a positively charged molecule that pairs with an anion in an ionic liquid via electrostatic interaction. Examples of cations suitable for inclusion in ionic liquids include, but are not limited to, ammonium, imidazolium, pyridinium, sulfonium, and phosphonium cations.

As used herein, the term "molar ratio" refers to the number of moles of one species in a mixture relative to the number of moles of a second species in the mixture. As a non-limiting example, an ionic liquid having an anion:cation ratio of 1:2 has at least two moles of the cation for every mole of the anion. For ionic liquids where the molar ratio of the anion to the cation is at least 1:2, the molar ratio can be, e.g., 1:2.1, 1:2.5, or 1:3, or 1:4.

As used herein, the term "choline" refers to the 2-hydroxy-N,N,N-trimethylethanamonium cation and salts thereof (e.g., 2-hydroxy-N,N,N-trimethylethanamonium hydroxide). The term "dicholine mucate," also referred to as $[Ch]_2[Mu]$, refers to an ionic liquid having mucic acid dianions and two choline cations for each of the mucic acid dianions. As used herein, the term "dicholine α-ketoglutarate," also referred to as $[Ch]_2[\alpha\text{-}Kg]$, refers to an ionic liquid having α-ketoglutaratic acid dianions and two choline cations for each of the α-ketoglutaratic acid dianions.

As used herein, the term "pH" refers to refers to a measurement of the concentration of hydrogen ions in a mixture such as an aqueous solution. pH is expressed as the decimal logarithm (i.e., $\log_{10}$) of the reciprocal of the hydrogen ion concentration in the mixture. The pH of a mixture can be determined using a number of known techniques. One of skill in the art will know how to adjust the pH of a mixture by adding acids and/or bases to the mixture.

As used herein, the term "acid" refers to a substance that is capable of donating a proton (i.e., a hydrogen cation) to form a conjugate base of the acid. Examples of acids include, but are not limited to, hydrochloric acid, sulfuric acid, acetic acid, and formic acid.

As used herein, the term "base" refers to a substance that is capable of accepting a proton (i.e., a hydrogen cation) to form a conjugate acid of the base. Examples of bases include, but are not limited to, sodium hydroxide, potassium hydroxide, sodium bicarbonate, and potassium carbonate.

As used herein, the terms "dissolve" and "dissolution" refer to the solvation of a solute with a solvent to form a solution. More particularly, dissolution refers to the partial or complete solubilization of biomass in an ionic liquid or an ionic liquid solution. In the methods of the invention, dissolution of lignocellulosic biomass can include partial or complete disruption of intra- and intermolecular hydrogen bonds present in cellulose polymer chains, partial or complete disruption of interactions between cellulose and hemicellulose, and partial or complete solubilization of lignin.

The terms "hydrolyze," "hydrolysis," and "saccharification," when used herein with respect to polysaccharide chemistry, refer to the cleavage of one or more glycosidic bonds in an oligosaccharide or a polysaccharide by water. The hydrolysis is typically catalyzed by an enzyme such as a glycoside hydrolase. Hydrolysis can also be promoted by addition of a catalyst such as an acid or base.

As used herein, the term "glycoside hydrolase" refers to an enzyme that catalyzes the cleavage of the glycosidic linkage in oligosaccharides or polysaccharides by water to release smaller sugars.

The terms "about" and "around," as used herein to modify a numerical value, indicate a close range surrounding that explicit value. If "X" were the value, "about X" or "around X" would indicate a value from 0.9X to 1.1X. "About X" thus includes, for example, a value from 0.95X to 1.05X, or from 0.98X to 1.02X, or from 0.99X to 1.01X. Any reference to "about X" or "around X" specifically indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.07X, 1.08X, 1.09X, and 1.10X. Accordingly, "about X" and "around X" are intended to teach and provide written description support for a claim limitation of, e.g., "0.98X."

II. Sugar-Based Ionic Liquids for Biomass Pretreatment and Saccharification

In one aspect, the present invention provides a method for preparing a sugar composition. In typical embodiments, a method of the invention, includes:
 i) forming a mixture including polysaccharide biomass and an ionic liquid solution, wherein
   the ionic liquid solution contains water and an ionic liquid, and
   the ionic liquid contains a) a cation and b) a sugar acid anion or a ketoacid anion;
 ii) maintaining the mixture under conditions sufficient to dissolve at least a portion of the polysaccharide present in the polysaccharide biomass;
 iii) adding at least one glycoside hydrolase to the mixture; and
 iv) maintaining the mixture containing the glycoside hydrolase under conditions sufficient to hydrolyze at least a portion of the dissolved polysaccharide, thereby forming the sugar composition;
wherein the sugar composition contains at least one monosaccharide or oligosaccharide.

Polysaccharide Biomass

The methods of the invention are used for the production of sugar compositions (containing monosaccharides, oligosaccharides, and/or polysaccharides) as chemical or fermentation feedstocks from biomass materials. The feedstocks, in turn, can be used for the production of ethanol, plastics, or other products or intermediates. Biomass can include, but is not limited to, wood resources, municipal solid waste, wastepaper, and crop residues (see, for example, Wiselogel et al., 1995, in Handbook on Bioethanol (Charles E. Wyman, editor), pp. 105-118, Taylor & Francis, Washington D.C.; Wyman, 1994, Bioresource Technology 50: 3-16; Lynd, 1990, Applied Biochemistry and Biotechnology 24/25: 695-719; Mosier et al., 1999, Recent Progress in Bioconversion of Lignocellulosics, in Advances in Biochemical Engineering/Biotechnology, T. Scheper, managing editor, Volume 65, pp. 23-40, Springer-Verlag, New York). Other examples of biomass include, without limitation, crops such as starch crops (e.g., corn, wheat, or barley), sugar crops (e.g., sugarcane, energy cane or sugar beet), forage crops (e.g., grasses, alfalfa, or clover), and oilseed crops (e.g., soybean, sunflower, or safflower); wood products such as trees, shrubs, or wood residues (e.g., sawdust, bark or the like from forest clearings and mills); waste products such as municipal solid waste (MSW; e.g., paper, food and yard wastes, or wood), process waste, and paper sludge; and aquatic plants such as algae, water weeds, water hyacinths, or reeds and rushes. Other examples of biomass include sorghum, rice hulls, rice straw, wheat straw, and other straws.

Accordingly, some embodiments of the invention provide a method for preparing a sugar composition as described above, wherein the polysaccharide biomass comprises cellulose, hemicellulose, lignocellulose, or mixtures thereof. In some embodiments, the polysaccharide biomass comprises lignocellulose.

Biomass materials typically contain a mixture of polysaccharide species. In many instances, the predominant polysaccharide in the primary cell wall of biomass is cellulose, the second most abundant is hemi-cellulose, and the third is pectin. The secondary plant cell wall, produced after the cell has stopped growing, also contains polysaccharides and is strengthened through polymeric lignin covalently cross-linked to hemicellulose.

Cellulose is a homopolymer of anhydrocellobiose and thus a linear β-(1-4)-D-glucan, while hemicelluloses include a variety of sugar subunits, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which helps stabilize the cell wall matrix.

In addition to the polysaccharides described above, polysaccharide biomass typically contains lignin. Lignin is a phenylpropane polymer of monolignol monomers. It is generally found as an integral part of the secondary cell walls of plants and certain types of algae. There are three monolignol monomers, methoxylated to various degrees: p-coumaryl alcohol, coniferyl alcohol, and sinapyl alcohol. These lignols are incorporated into lignin in the form of the phenylpropanoids p-hydroxyphenyl (H), guaiacyl (G), and syringyl (S), respectively. Gymnosperms have a lignin that consists almost entirely of G with small quantities of H. That of dicotyledonous angiosperms is more often than not a mixture of G and S (with very little H), and monocotyledonous lignin is a mixture of all three. Many grasses have mostly G, while some palms have mainly S. All lignins contain small amounts of incomplete or modified monolignols, and other monomers are prominent in non-woody plants. Unlike cellulose and hemicellulose, lignin cannot be depolymerized by hydrolysis. Cleavage of the principal bonds in the lignin polymer generally proceeds through oxidation.

In some embodiments, the polysaccharide biomass is derived from corn stover, corn fiber, hard wood, softwood, cereal straw, switchgrass, Miscanthus, rice hulls, municipal solid waste (MSW), industrial organic waste, office paper, or mixtures thereof.

Ionic Liquids

A number of ionic liquids can be used in the methods of the invention. In general, the ionic liquid is suitable for pretreatment of the biomass and compatible with glycoside hydrolases used for saccharification of cellulose and other polysaccharides. The ionic liquids contain a sugar acid ion paired with cations via electrostatic interactions. In certain embodiments, the ionic liquid used for biomass pretreatment contains one sugar acid dianion paired with two cations.

Any suitable sugar acid can be used in the methods of the invention. The sugar acids can be derived from lignocellulosic biomass hydrolysates rich in glucose and xylose or from any other sugar present in biomass, such as galactose, arabinose, mannose, or the like, or a mixture thereof. In some embodiments, the sugar acid is a $C_6$ sugar acid or a $C_5$ sugar acid, or a mixture thereof.

In some embodiments, the sugar acid is selected from the group consisting of an aldaric acid, an aldonic acid, a uronic acid, and combinations thereof. In some embodiments, the sugar acid is selected from the group consisting of mucic acid [i.e., (2S,3R,4S,5R)-2,3,4,5-tetrahydroxyhexanedioic acid; meso-galactaric acid]; saccharic acid [i.e., (2S,3S,4S, 5R)-2,3,4,5-tetrahydroxyhexanedioic acid; D-glucaric acid]; D-xylaric acid [i.e., (2R,4S)-2,3,4-trihydroxypentanedioic acid]; D-arabinaric acid [i.e., (2S,4S)-2,3,4-trihydroxypentanedioic acid], and mannaric acid [i.e., (2S,3S,4S,5S)-2,3, 4,5-tetrahydroxyhexanedioic acid].

Any ketoacid can be used in the methods of the invention. Like sugar acids, ketoacids can be derived from lignocellulosic biomass. In some embodiments, the ketoacid is a $C_6$ ketoacid or a $C_5$ ketoacid, or a mixture thereof. Examples of ketoacids for use in the ionic liquids and methods of the invention include, but are not limited to, α-ketoglutaric acid, pyruvic acid, acetoacetic acid, levulinic acid, and the like.

In some embodiments, the anion in the ionic liquid is selected from the group consisting of a mucic acid anion, a mucic acid dianion, an α-ketoglutaric acid anion, and an α-ketoglutaric acid dianion.

The ionic liquids used in the methods of the invention can contain any suitable cation. Suitable cations include, but are not limited to, ammonium cations and imidazolium cations. Examples of ammonium cations include, but are not limited to, 2-hydroxyethyl-trimethylammonium, benzyldimethyltetradecylammonium, benzyltrimethylammonium, butyltrimethylammonium, choline, diethylmethyl(2-methoxyethyl) ammonium, ethyldimethylpropylammonium, methyltrioctadecylammonium, methyltrioctylammonium, tetrabutylammonium, tetradodecylammonium, tetraethylammonium, tetraheptylammonium, tetrahexadecylammonium, tetrahexylammonium, tetrakis(decyl)ammonium, tetramethylammonium, tetraoctylammonium, tributylmethylammonium, triethylmethylammonium, and tris(2-hydroxyethyl)methylammonium.

The imidazolium cations can be, but are not limited to, 1-alkyl-3-alkylimidazolium cations, wherein an "alkyl" is an alkyl group comprising from 1 to 10 carbon atoms. In some embodiments, the "alkyl" is a methyl group, ethyl group or butyl group. Examples of imidazolium cations include: 1-(2-hydroxyethyl)-3-methylimidazolium; 1-(3-cyanopropyl)-3-methylimidazolium; 1,2,3-trimethylimidazolium; 1,2-dimethyl-3-propylimidazolium; 1,3-bis(cyanomethyl) imidazolium; 1,3-diethoxyimidazolium; 1,3-dihydroxy-2-methylimidazolium; 1,3-dihydroxyimidazolium; 1,3-dimethoxy-2-methylimidazolium; 1,3-dimethoxyimidazolium; 1,3-dimethylimidazolium; 1-allyl-3-methylimidazolium; 1-benzyl-3-methylimidazolium; 1-butyl-2,3-dimethylimidazolium; 1-butyl-3-methylimidazolium (BMIM); 1-decyl-3-methylimidazolium; 1-dodecyl-3-methylimidazolium; 1-ethyl-2,3-dimethylimidazolium (EDIM); 1-ethyl-3-methylimidazolium (EMIM); 1-hexyl-3-methylimidazolium; 1-methyl-3-octylimidazolium; 1-methyl-3-propylimidazolium; 1-methylimidazolium (MIM); and 4-(3-butyl-1-imidazolio)-1-butanesulfonate.

Other cations can be used in the ionic liquids of the present invention, including, but not limited to: pyridinium cations (e.g., N-ethylpyridinium, N-butylpyridinium, and the like); sulfonium cations (e.g., trimethylsulfonium, triethylsulfonium, tributylsulfonium, diethylmethylsulfonium, dimethylpropylsulfonium, dimethylhexylsulfonium, and the like); and phosphonium cations (e.g., tetramethylphosphonium, tetraethylphosphonium, tetrapropylphosphonium, tetrabutylphosphonium, tetraoctylphosphonium, tetraphenylphosphonium, trimethylethylphosphonium, triethylmethylphosphonium, hexyltrimethylphosphonium, trimethyloctylphosphonium, and the like).

In some embodiments, the cation is selected from choline, $(C_{1-18}$ alkyl$)_3$NH$^+$, $(C_{1-6}$ alkyl$)_x(C_{6-18}$ alkyl$)_y$N$^+$, $(C_{1-10}$ alkyl$)_z$imidazolium, $(C_{1-10}$alkyl$)_z$pyrazolium, and mixtures thereof; wherein subscript x and subscript y are each 0, 1, 2, 3, or 4, and the sum of x and y is 4; and wherein each subscript z is 1, 2, or 3.

The cation be, for example, $(C_{1-16}$ alkyl$)_3$NH$^+$, $(C_{1-17}$ alkyl$)_3$NH$^+$, $(C_{1-10}$ alkyl$)_3$NH$^+$, $(C_{1-8}$ alkyl$)_3$NH$^+$, $(C_{1-6}$ alkyl$)_3$NH$^+$, $(C_{12-18}$ alkyl$)_3$NH$^+$, or $(C_{16-18}$ alkyl$)$ NH$^+$. The cation be $(C_{1-3}$ alkyl$)_x(C_{6-12}$ alkyl$)_y$N$^+$ or $(C_{1-2}$ alkyl$)_x(C_{6-8}$alkyl$)_y$N$^+$, wherein subscript x and subscript y are each 0, 1, 2, 3, or 4, and the sum of x and y is 4. The cation can be $(C_{1-8}$ alkyl$)_z$ imidazolium, $(C_{1-6}$ alkyl$)_z$imidazolium, $(C_{1-8}$ alkyl$)_z$pyrazolium, or $(C_{1-6}$ alkyl$)_z$pyrazolium, wherein each subscript z is 1, 2, or 3.

In some embodiments, the cation is selected from 1-ethyl-3-methylimidazolium, 1-butyl-3-methylimidazolium, 1-ethyl-2,3-dimethylimidazolium, tris(2-hydroxyethyl) methylammonium, 1-methylimidazolium, 1,2,4-trimethylpyrazolium, triethylammonium, tributylmethylammonium, hexadecyltrimethylammonium, myristyltrimethylammonium, tridodecylmethylammonium, trimethyloctadecylammonium, and choline. In some embodiments, the cation is choline.

The ionic liquids used in the methods of the invention can be prepared by combining a sugar acid, or a salt thereof, with a salt containing the cation to be incorporated into the ionic liquid. The sugar acid and the cation can be combined as solutions in water or in a suitable organic solvent. As a non-limiting example, one equivalent of mucic acid in aqueous solution can be combined with two equivalents of choline hydroxide in aqueous solution. Water can be removed at elevated temperature and/or under reduced pressure. Water-miscible co-solvents, including but not limited to methanol, acetonitrile, acetone, and the like, can be used to precipitate excess anions or cations for removal by centrifugation or filtration. Impurities can be removed by passing the ionic liquid through activated charcoal, polymeric ion-exchange resins, or other decolorizing agents.

In general, the molar ratio of the sugar acid anions in the ionic liquid solution to the cations in the ionic liquid solution will be sufficient to provide a solution pH of at least about 7. In certain embodiments, the molar ratio of the sugar acid anion to the cation is at least about 1:2. The molar ratio of the sugar acid anion to the cation can be, for example, at least 1:1.8, or at least 1:1.9; or at least 1:2, or at least 1:2.1 or at least 1:2.2. When the mixture of the sugar acid and the salt is made in aqueous solution, the pH of the resulting ionic liquid solution will be basic. In general, the pH of the ionic liquid solution is above 7. The pH of the ionic liquid solution can be, for example, at least 7, at least 7.5, at least 8, at least 8.5, at least 9, at least 9.5, at least 10, at least 10.5, at least 11, at least 11.5, at least 12, at least 12.5, at least 13, or at least 13.5, In certain embodiments, one equivalent of a sugar acid or ketoacid is combined with two equivalents of a salt containing a cation and a basic anion. As a non-limiting example, combination of one equivalent of mucic acid with two equivalents of choline hydroxide in aqueous solution will result in an ionic liquid solution having a pH of about 13.5. One of skill in the art will appreciate that the pH of the ionic liquid solution will vary depending on the particular sugar acid and cation used, the ratio of the sugar acid and the cation, and their absolute concentrations.

As described in more detail below, the pH of mixture containing the ionic liquid solution can be reduced after the pretreatment step so that mixture is compatible with enzymes, such as cellulases, used to break down the pretreated biomass. In certain embodiments, the pH is reduced by adding the same sugar acid that is present in the ionic liquid. Accordingly, in some embodiments an ionic liquid solution having a pH of at least about 10 (e.g., from about 10.5 to about 13.5) is obtained by combining one equivalent of a sugar acid or ketoacid with two equivalents of a salt containing a cation; the pH of the ionic liquid solution is then reduced to below about 7 via addition of a second equivalent of the acid prior to the introduction of enzymes such as glycoside hydrolases.

In some embodiments an ionic liquid solution having a pH greater than 7 (e.g., at least 10) is obtained by combining one equivalent of mucic acid with two equivalents of choline hydroxide. After pretreatment of the polysaccharide biomass, the pH of the ionic liquid solution is then reduced to below about 7 (e.g., around 5) via addition of a second equivalent of mucic acid prior to the introduction of enzymes such as glycoside hydrolases.

In some embodiments an ionic liquid solution having a pH greater than 7 (e.g., a pH of at least about 10) is obtained by combining one equivalent of α-ketoglutaric acid with two equivalents of choline hydroxide. After pretreatment of the polysaccharide biomass, the pH of the ionic liquid solution is then reduced to below about 7 (e.g., around 5) via addition of a second equivalent of α-ketoglutaric acid prior to the introduction of enzymes such as glycoside hydrolases.

The pH of an ionic liquid solution can be raised or lowered as necessary by adding bases, such as sodium hydroxide or potassium hydroxide, and acids, such as hydrochloric acid or sulfuric acid, to the ionic liquid solution. As a non-limiting example, combination of one equivalent of mucic acid with one equivalent of choline hydroxide in aqueous solution fbllowed by the addition of potassium hydroxide can provide an ionic liquid having a pH of about 11.

The ionic liquid solution contain any suitable amount of water. In general, the ionic liquid solutions used in the methods of the invention contain from about 0.1% water to about 95% water by weight of the ionic liquid solution. An ionic liquid solution can contain, for example, from about 5% to about 90% water, or from about 10% to about 80% water, or from about 20% to about 60% water, or from about 30% to about 50% water, or from about 0.1 to about 50% water, or from about 5% to about 45% water, or from about 10% to about 40% water, or from about 15% to about 35% water, or from about 20% to about 30% water by weight of the ionic liquid solution. The ionic liquid solution can contain about 0.1, 1, 5, 10, 15, 20, 25, 30, 35, 40, 45, 50, 55, 60, 65, 70, 71, 72, 73, 74, 75, 76, 77, 78, 79, 80, 81, 82, 83, 84, 85, 86, 87, 88, 89, 90, 91, 92, 93, 94, or about 95% water by weight of the ionic liquid solution.

In certain embodiments, the ionic liquid solution contains from about 50% (w/w) to about 95% (w/w) water. The ionic liquid solution can contain from about 50% to about 55% water, or from about 55% to about 60% water, or from about 60% to about 65% water, or from about 65% to about 70% water, from about 70% to about 75% water, or from about 75% to about 80% water, or from about 80% to about 85% water, or from about 85% to about 90% water, or from about 90% to about 95% water by weight of the ionic liquid solution. The ionic liquid solution can contain from about 70% to about 90% water, or from about 72% to about 85% water, or from about 73% to about 80% water by weight of the ionic liquid solution. The ionic liquid solution can contain from about 70% to about 95% water, or from about 80% to about 93% water, or from about 85% to about 92% water by weight of the ionic liquid solution. In such embodiments, the ionic liquid solution will contain from about 30% (w/w) to about 5% (w/w) ionic liquid. The ionic liquid solution can contain from about 25% to about 30% ionic liquid, or from about 20% to about 25% ionic liquid, or from about 15% to about 20% ionic liquid, or from about 10% to about 15% ionic liquid, or from about 5% to about 10% ionic liquid by weight of the ionic liquid solution. The ionic liquid solution can contain from about 10% to about 30% ionic liquid, or from about 15% to about 28% ionic liquid, or from about 20% to about 27% ionic liquid by weight of the ionic liquid solution. The ionic liquid solution can contain from about 5% to about 30% ionic liquid, or from about 7% to about 20% ionic liquid, or from about 8% to about 15% ionic liquid by weight of the ionic liquid solution.

Other amounts of water and ionic liquid can be used in the methods of the invention, depending in part on factors such as the type of biomass material to be treated and the particular cations and anions to be included in the ionic liquid.

In some embodiments, the ionic liquid solution contains:
about 50-90% (w/w) water; and
about 10-50% [sugar acid anion][cation] (w/w).
In some embodiments, the ionic liquid solution contains:
about 50-90% (w/w) water; and
about 10-50% 1:2 [sugar acid anion][cation] (w/w).
In some embodiments, the ionic liquid solution contains:
about 50-90% (w/w) water; and
about 10-50% [mutate di-anion][cation] (w/w).
In some embodiments, the ionic liquid solution contains:
about 50-90% (w/w) water; and
about 10-50% 1:2 [α-ketoglutarate di-anion][cation] (w/w).
In some embodiments, the ionic liquid solution contains:
about 50-90% (w/w) water; and
about 10-50% dicholine mucate (w/w).
In some embodiments, the ionic liquid solution contains:
about 50-90% (w/w) water; and
about 10-50% dicholine α-ketoglutarate (w/w).

The pretreatment mixture can contain any suitable amount of polysaccharide biomass. In general, the pretreatment mixture contains up to about 50% biomass by weight of the pretreatment mixture. The pretreatment mixture can contain, for example, from about 0.1 to about 50% biomass, or from about 5% to about 45% biomass, or from about 10% to about 40% biomass, or from about 15% to about 35% biomass, or from about 20% to about 30% biomass, or from about 5% to about 40% biomass, or from about 5% to about 30% biomass, or from about 5% to about 20% biomass, or from about 5% to about 10% biomass by weight of the pretreatment mixture. The pretreatment mixture can contain about 1, 5, 10, 15, 20, 25, 30, 35, 40, 45, or 50% biomass by weight of the pretreatment mixture. In some embodiments, the mixture includes from about 5% (w/w) to about 30% (w/w) polysaccharide biomass. Other amounts of biomass can be used in the methods of the invention, depending in part on factors such as the type of biomass material and the particular ionic liquid used in the method.

Biomass Pretreatment

Pretreatment of the polysaccharide biomass in the ionic liquid solution can be conducted thr any suitable length of time at any suitable temperature and pressure. In general, pretreatment is conducted for anywhere from a few minutes to several hours. Pretreatment can be conducted, for example, for about five minutes, or about 10 minutes, or about 30 minutes, or about 60 minutes. Pretreatment can be conducted for about 1, 1.5, 2, 2.5, 3, 3.5, 4, 4.5, 5, 5.5, 6, 9, 12, 15, 18, 21, 24, 36, 48, 60, or about 72 hours. Pretreatment is generally conducted at a temperature ranging from about 20° C. to about 200° C. Pretreatment can be conducted, for example, at a temperature ranging from about 20° C. to about 100° C., or from about 40° C. to about 80° C., or from about 100° C. to about 200° C., or from about 120 CC to about 180° C., or from about 140° C. to about 160° C., or from about 40° C. to about 180° C., or from about 60° C. to about 160° C., or from about 80° C. to about 140° C. or from about 100 to about 120° C. Pretreatment can be conducted at about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or about 200° C. for at least about 0.5, 1, 3, 6, 9, 12, or 16 hours. Pretreatment can be conducted at atmospheric pressure or elevated pressures. Pretreatment can be conducted, for example, at a pressure (Pg) ranging from about 14 psi to about 4000 psi, or from about 14 psi to about 3500 psi, or from about 14 psi to about 2500 psi, or from about 14 psi to about 1500 psi in certain embodiments, the pretreatment is conducted at around atmospheric pressure (i.e. 14.696 psi).

In some embodiments, the invention provides a method for preparing a sugar composition as described above wherein step ii) includes maintaining the mixture of step i) at a temperature of at least about 100° C. for at least about 30 minutes.

Biomass Saccharification

Following pretreatment of the polysaccharide biomass, the pH of the mixture containing the dissolved polysaccharide and the ionic liquid solution is reduced to a level that is suitable for enzymatic hydrolysis of the polysaccharide by one or more glycoside hydrolases. In general, the pH of mixture is reduced to at most about 7. The pH of the mixture can be reduced, for example, to less than 7, less than 6.5, less than 6, less than 5.5, or less than 5. In certain embodiments, the pH of the mixture is reduced to a pH of from about 5 to about 6.

The pH of the mixture containing the dissolved polysaccharide can be reduced by adding an acid to the mixture. Any suitable acid can be used to reduce the pH. Suitable acids include, but are not limited to, hydrochloric acid, sulfuric acid, nitric acid, acetic acid, citric acid, formic acid, and the like. In certain embodiments, the acid used for reducing the pH of the mixture containing the dissolved polysaccharide is the same sugar acid that is present in the ionic liquid. In certain such embodiments, the mixture containing the dissolved polysaccharide and the ionic liquid solution is combined with one molar equivalent of the sugar acid (with respect to the amount of the sugar acid present in the ionic liquid). As a non-limiting example, combination of one equivalent of mucic acid with a mixture containing dissolved polysaccharide and dicholine mucate will reduce the pH of the mixture to between about 5 and about 6. Further adjustments to the pH can be made by adding further amounts of acid (e.g., hydrochloric acid) to the mixture as necessary. One of skill in the art will appreciate that the pH of the mixture containing the dissolved polysaccharide can be adjusted to maximize the activity of an enzyme, or a mixture of enzymes, e.g., one or more glycoside hydrolases, used in the subsequent hydrolysis step. The particular pH will depend in part on factors including, but not limited to, the specific glycoside hydrolase(s) and the amount of ionic liquid in the mixture.

Accordingly, some embodiments of the invention provide a method for preparing a sugar composition as described above, which further comprises step ii-b): reducing the pH of the mixture containing the dissolved polysaccharide to less than 7 prior to adding the glycoside hydrolase in step iii). In some embodiments, step ii-b) includes adding an acid to the mixture resulting from step ii). In some such embodiments, the acid used in step ii-b) is the same sugar acid used in step i). In some such embodiments, the molar amount of acid in step ii-b) is equal to the molar amount of acid in step i).

The methods of the invention generally include adding on or more enzymes that break down polysaccharide biomass into smaller components. Typically, the pretreated biomass is subjected to the action of one, or multiple, enzyme activities selected from a protease, a lipase, a cellulose, an amylase, a glucano-hydrolase, a pectinase, a xylanase, a ferulic acid esterase, and a mannanase. The pretreated biomass may also be treated with other enzymes, hemicellulases, that are used for the degradation of biomass.

In some embodiments, the glycoside hydrolase is selected from an endoglucanase, an exoglucanase, a β-glucosidase, a xylanase, and mixtures thereof. In some embodiments, one or more cellulases are added to the pretreated biomass present in the ionic liquid mixture in which the pH has been reduced, e.g., to at least about 7, following treatment at a high pH.

A "cellulase" as used herein is a glycoside hydrolase enzyme that hydrolyzes cellulose (β-1,4-glucan or β-D-glucosidic linkages) resulting in the formation of glucose, cellobiose, cellooligosaccharides, and the like. In the context of the present invention, cellulases include endoglucanases, exoglucanases or cellobiohydrolases; and β-glucosidases. Endoglucanases (EC 32.1.4) including endo-1,4-β-glucanases or 1,4-β-D-glucan-4-glucanohydrolases, act randomly on soluble and insoluble 1,4-β-glucan substrates. Exoglucanases (exo-1,4-β-D-glucanases, e.g., the 1,4-β-D-glucan glucohydrolases, EC 3.2.1.74) liberate D-glucose from 1,4-β-D-glucans and hydrolyze D-cellobiose Cellobiohydrolases (1,4-β-D-glucan cellobiohydrolases, EC 3.2.1.91) liberate D-cellobiose from 1,4-β-glucans. β-Glucosidases ([β]-D-glucoside glucohydrolase; β-D-glucosidases; EC 3.2.1.21) act to release D-glucose units from cellobiose and soluble cellodextrins, as well as an array of glycosides. Endoglucanases act mainly on the amorphous parts of the cellulose fiber, whereas cellobiohydrolases are also able to degrade crystalline cellulose.

A combination of two or more cellulases can be used in the methods of the invention. Cellulases act in concert to catalyze the hydrolysis of cellulose-containing substrates. For example, endoglucanases break internal bonds and disrupt the crystalline structure of cellulose, exposing individual cellulose polysaccharide chains ("glucans"). Cellobiohydrolases incrementally shorten the glucan molecules, releasing, mainly cellobiose units (a water-soluble β-1,4-linked dimer of glucose) as well as glucose, cellotriose, and cellotetrose. β-glucosidases split the cellobiose into glucose monomers. The cellulase can be a thermostable cellulase. In certain embodiments the glycoside hydrolase, such as a cellulase, is selected such that it can perform optimally in the presence of ionic liquid.

A xylanase and/or a "mannanase" may also be employed in the saccharification of pretreated biomass. A "xylanase" is a glycoside hydrolase enzyme that catalyzes the endohydrolysis of 1,4-β-D-xylosidic linkages in xylans. Xylanases include enzymes classified as a 1,4-β-D-xylan-xylohydrolase (E.C. 3.2.1.8).

A "mannanase" is a glycoside hydrolase that hydrolyzes 1,4-β-D-mannosidic linkages in mannans, galactomannans and/or glucomannans. "Mannanase activity" refers to hydrolysis of 1,4-β-D-mannosidic linkages in mannans, galactomannans and/or glucomannans. Mannases include enzymes classified as EC 3.2.1.78.

Cellulases suitable for use in the present invention are commercially available from, for example, Genencor (USA) and Novozymes (Europe). For instance, Novozyme has a number of different enzymes and enzyme complexes that are specifically designed to be useful for the hydrolysis of lignocellulosic materials. Examples include, but are not limited to, the following: NS50013, which is a cellulase; NS50010, which is a β-glucosidase, NS22086, which is a cellulase complex; NS22086, which is a xylanase; NS22118, which is β-glucosidase; NS22119, which is an enzyme complex of carbohydrases, including arabinase, β-glucanase, cellulase, hemicellulase, pectinase, and xylanase; NS22002, which is a mixture of β-glucanase and xylanase; and NS22035, which is a glucoamylase. In addition, suitable thermostable cellulases are disclosed in International Pat. Appl. Pub. No. WO 2010/124266, which is incorporated herein by reference. Other hydrolases suitable for hydrolyzing the pretreated biomass, i.e., the lignocellulosic material, will be known to those of skill in the art. See e.g., Viikari et al., $Adv.$ $Biochem.$ $Eng.$ $Biotechnol.$, 108:121-45, 2007; and U.S. Pat. Appl. Pub Nos. US 2009/0061484; US 2008/0057541; and US 2009/0209009, which are incorporated herein by reference.

Any suitable amount of enzyme or enzyme mixture, e.g., glycoside hydrolase or mixture of glycoside hydrolases, can be used in the methods of the invention. In general a sub-stoichiometric amount of the glycoside hydrolase, with respect to the dissolved polysaccharide, is used. The amount of glycoside hydrolase can be expressed as activity units. Alternatively, the amount of the glycoside hydrolase used in the methods of the invention can be expressed relative to the amount of biomass treated in the pretreatment step. For example, the hydrolysis mixture can contain a glycoside hydrolase (or a mixture of glycoside hydrolases) in an amount ranging from about 0.01 to about 10% (w/w), with respect to the amount of biomass used in the pretreatment step. Thus, for example, when method is conducted using 1 kg of biomass, for example, the hydrolysis step can be conducted with a glycoside hydrolase or a mixture of glycoside hydrolases in an amount ranging from about 100 mg to about 100 g. Those of skill in the art will appreciate that the amount of glycoside hydrolase or mixture of enzymes used in the methods of the invention will depend in part on factors including, but not limited to, the particular enzyme used, the nature of the biomass source, and the extent of the pretreatment step.

The enzymatic hydrolysis step can be conducted for any length of time any suitable temperature. The enzymatic hydrolysis step can be conducted, for example, for about 2, 5, 10, 15, 30, 45, or 60 minutes. The enzymatic hydrolysis step can be conducted for about 1, 1,5, 2, 2.5, 3, 3.5, 4, 4.5, 5, 5.5, 6, 9, 12, 15, 18, 21, 24, 30, 36, 42, 48, or 72 hours.

Enzymatic hydrolysis is generally conducted at a temperature ranging from about 20° C. to about 60° C. Enzymatic hydrolysis can be conducted, for example, at a temperature ranging from about 20° C. to about 40° C., or from about 40° C. to about 60° C. Enzymatic hydrolysis can be conducted at about 25° C., about 37° C., or about 55° C. for at least about 10, 20, 30, 60, or 90 minutes or for at least about 2, 3, 4, 5, 7, 8, 9, 10, 11, 12, 24, 48, or 72 hours.

Sugar Compositions

The methods of the invention provide sugar compositions containing one or monosaccharides and/or oligosaccharides. Monosaccharides present in the sugar compositions can include, but are not limited to, fucose, arabinose, rhamnose, galactose, mannose, xylose, glucose, glucuronic acid, and galacturonic acid. The oligosaccharides in the sugar compositions contain monosaccharide subunits (e.g., fucose, arabinose, rhamnose, galactose, mannose, xylose, glucose, glucuronic acid, and galacturonic acid) linked together via glycosidic bonds. Typically, between about 10% and about 100% conversion of the polysaccharide biomass to sugars results from the methods of the invention. Thus, e.g., processing of 1 kg of polysaccharide biomass according to the methods of the invention can yield from about from about 110 g to about 1100 g of the constituent monosaccharides and oligosaccharides in the final sugar compositions. For example, processing of 1 kg of switchgrass according to the methods of the invention can yield sugar compositions containing from about 0.1 g to about 350 g of glucose and from about 0.1 g to about 210 g to xylose. One of skill in the art will appreciate that the components and the yield of the sugar composition will depend, in part, on the specific source of the biomass and the specific conditions that are used for pretreatment and hydrolysis.

Sugar compositions obtained using the methods of the invention can be used as carbon sources for host cells to produce useful organic compounds such as biofuels. The sugar compositions can be used for the production of fermentation products (e.g., ethanol, tartaric acid, itaconic acid, succinic acid, propanediol, butanol, glycerol, and the like) as described, for example, in International Pat. Appl. Pub. No. WO 2016/070125, which is incorporated herein by reference.

Ionic Liquid Recycling

The methods of the invention allow for simple recycling of the ionic liquid from one form to another for re-use. This is particularly true for embodiments wherein the same acid (e.g., mucic acid) is used in the pretreatment step and the pH reduction step. The pretreatment step is performed in the basic stoichiometry, and then the solution is acidified for the enzymatic hydrolysis step. After the hydrolysis, the soluble sugars can be removed by any of the previously reported methods. For example, if a liquid-liquid extraction with boronic acids is used, the solution can be 'switched' back to the basic form first, which matches the conditions required for efficient extraction [Brennan, et al. 2010. BioEnergy Research 3: 123-33; Shi, et al. 2013. Green Chemistry 15: 2579-89]. After extraction, the IL-phase can be recycled to pretreat another batch of biomass. Alternatively, the hydrolysate can be fed directly into the fermentation step. In certain embodiments, E. coli, or a yeast, e.g., S. cerevisiae, or other microorganisms can tolerate high concentrations of the hydrolysate produced by this process, limiting the dilution required.

The biomass input, glucose and xylose output, and the insoluble lignin/ash output can be measured for the methods of the invention, and a biomass mass balance for the pretreatment and saccharification steps can be constructed from these streams. Nearly 76% of the original biomass leaves the reactor in the liquid stream.

III. Examples

Example 1. Preparation of Choline Mucate Ionic Liquids and Use Thereof

In a typical process, choline hydroxide ([Ch][OH], 46 wt % in $H_2O$) is taken in a glass beaker with a magnetic stiffer, with continuous stirring. Mucic acid (40 wt % in $H_2O$) is added dropwise at room temperature until the pH of the resulting IL reaches 13.5. At this point, the resulting dicholine mucate ionic liquid (i.e., $[Ch]_2[Mu]$) contains two molar equivalents of choline cations and one molar equivalent of mucate anions. $[Ch]_2[Mu]$ (40 wt % in $H_2O$) is used for further pretreatment.

$[Ch]_2[Mu]$ is then used for one-pot pretreatment and saccharification. In an integrated process, 1 g switchgrass is mixed with 9 g $[Ch]_2[Mu]$ (40 wt % in $H_2O$) at a 10 wt % biomass loading in a 35 mL pressure tube and pretreated at 140° C. for 1 h. After pretreatment, the slurry is diluted with DI-water to obtain a final $[Ch]_2[Mu]$ concentration of 20 wt %. Before adding enzyme mixture (CTec2/HTec2=9:1, v/v) for saccharification, mucic acid (40 wt % in $H_2O$) is added to the slurry to reduce the pH of the system to 5. In some instances, citrate buffer can be added into the system (e.g., at a concentration of 50 mM) to maintain the mixture at the desired pH. Enzymatic hydrolysis is conducted at 50° C. in a 50 mL plastic tubes for 3 days with an enzyme loading of 10 mg protein/g switchgrass. The glucose yield is 76.3% and xylose yield is 49.6%.

Figure 1:
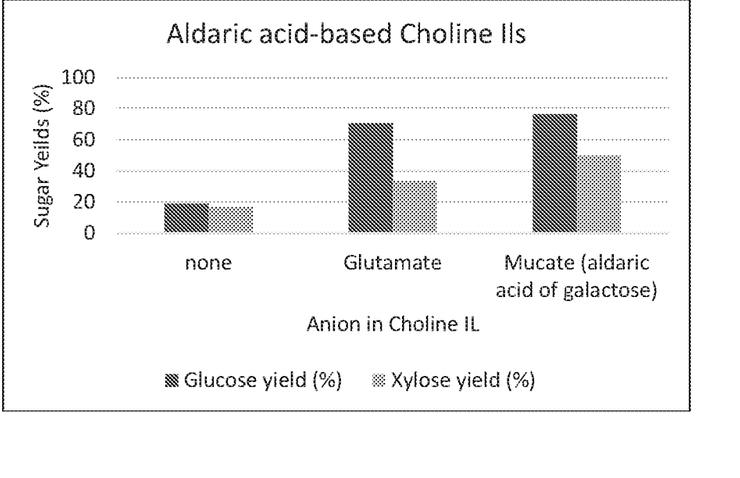
FIG. 1 shows a comparison of sugar yield resulting from one-pot pre-treatment and saccharification of switch grass using an aldaric acid-based choline ionic liquid, [Ch]$_2$[Mu], and using [Ch]$_2$[glutamate].

FIG. 1 shows a comparison of sugar yield resulting from one-pot pre-treatment and saccharification of switch grass using an aldaric acid-based choline ionic liquid, $[Ch]_2[Mu]$, and using $[Ch]_2[glutamate]$. Advantageously, the sugar compositions can be prepared in good yield using sugar-derived ionic liquids for biomass pretreatment and saccharification. Because the ionic liquids can be prepared with inexpensive materials that are readily available at biorefineries, the expense associated with non-lignocellulosic materials (e.g., glutamic acid-based ionic liquids) can be reduced or eliminated.

Example 2. Preparation of $[Ch][\alpha\text{-Kg}]$ and Use Thereof

In a typical process, choline hydroxide ([Ch][OH], 46 wt % in $H_2O$) is mixed with α-ketoglutaric acid (40 wt % in $H_2O$) at room temperature until the pH reaches 13.5. At this point, the resulting dicholine ketoglutarate ionic liquid (i.e., $[Ch]_2[\alpha\text{-Kg}]$) contains two molar equivalents of choline cations and one molar equivalent of mucate anions.

$[Ch]_2[\alpha\text{-Kg}]$ is then used for one-pot pretreatment and saccharification. In an integrated process, 40 g corn stover (2 mm particle size) is mixed with 160 g $[Ch]_2[\alpha\text{-Kg}]$ (40 wt % in $H_2O$)) at a 20 wt % biomass loading in a 300 mL Parr reactor and pretreated at 120° C. for 4 h. After pretreatment, the slurry is diluted with DI-water to obtain a final IL concentration of 10 wt %. Before adding enzyme mixture (CTec2/HTec2=9: v/v) for the saccharification, α-Ketoglutaric acid (40 wt % in $H_2O$) is used to drop and maintain the pH of the system to 5. Enzymatic hydrolysis is conducted at 50° C. in a IL shake flask for 3 days with an enzyme loading is 20 mg protein/g corn stover.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for preparing a sugar composition, the method comprising:
   i) forming a mixture comprising polysaccharide biomass and an ionic liquid solution, wherein
      the ionic liquid solution comprises water and an ionic liquid, and the ionic liquid comprises a) a cation and b) an anion, wherein the anion is selected from the group consisting of a mucic acid anion, a saccharic acid anion, a xylaric acid anion, an arabinaric acid anion, a mannaric acid anion, an α-ketoglutaric acid anion, and a levulinic acid anion;
   ii) maintaining the mixture under conditions sufficient to dissolve at least a portion of the polysaccharide present in the polysaccharide biomass;
   iii) adding at least one glycoside hydrolase to the mixture; and
   iv) maintaining the mixture containing the glycoside hydrolase under conditions sufficient to hydrolyze at least a portion of the dissolved polysaccharide, thereby forming the sugar composition;
   wherein the sugar composition comprises at least one monosaccharide or oligosaccharide.

2. The method of claim 1, wherein the anion is selected from the group consisting of a mucic acid anion, a saccharic acid anion, a xylaric acid anion, an arabinaric acid anion, and a mannaric acid anion.

3. The method of claim 1, wherein the anion is selected from the group consisting of an α-ketoglutaric acid anion, and a levulinic acid anion.

4. The method of claim 1, wherein the anion is selected from the group consisting of a mucic acid anion and an α-ketoglutaric acid anion, wherein the mucic acid anion is a mucic acid dianion, and wherein the α-ketoglutaric acid anion is an α-ketoglutaric acid dianion.

5. The method of claim 1, wherein the cation is selected from the group consisting of choline, $(C_{1-18}\ alkyl)_3NH^+$, $(C_{1-6}\ alkyl)_x(C_{6-18}\ alkyl)_yN^+$, $(C_{1-10}\ alkyl)_z$imidazol-ium, $(C_{1-10}\ alkyl)_z$pyrazolium, and mixtures thereof; wherein subscript x and subscript y are each 0, 1, 2, 3, or 4, and the sum of x and y is 4; and wherein each subscript z is 1, 2, or 3.

6. The method of claim 1, wherein the ionic liquid solution comprises from about 25% (w/w) to about 95% (w/w) water.

7. The method of claim 1, wherein the mixture in step i) comprises from about 5% (w/w) to about 30% (w/w) polysaccharide biomass.

8. The method of claim 1, wherein step ii) comprises maintaining the mixture of step i) at a temperature of at least about 100° C. for at least about 30 minutes.

9. The method of claim 1, wherein the pH of the mixture in step i) is greater than 7.

10. The method of claim 9, further comprising:
    ii-b) reducing the pH of the mixture containing the dissolved polysaccharide to less than 7 prior to adding the glycoside hydrolase in step iii).

11. The method of claim 10, wherein step ii-b) comprises adding an acid to the mixture resulting from step ii).

12. The method of claim 11, wherein the acid used in step ii-b) is the same sugar acid or ketoacid used in step i).

13. The method of claim 1, wherein the polysaccharide biomass comprises cellulose, hemicellulose, lignocellulose, or mixtures thereof.

14. The method claim 1, wherein the glycoside hydrolase is a cellulase, an endoglucanase, an exoglucanase, a β-glucosidase, a xylanase, or a mixture thereof.

* * * * *